(12) United States Patent
Mouradian

(10) Patent No.: US 10,117,598 B1
(45) Date of Patent: Nov. 6, 2018

(54) NON-INVASIVE WEARABLE RESPIRATION RATE MONITORING SYSTEM

(71) Applicant: SENSOGRAM TECHNOLOGIES, INC., Plano, TX (US)

(72) Inventor: Vahram Mouradian, Plano, TX (US)

(73) Assignee: Sensogram Technologies, Inc., Plano, TX (US)

( * ) Notice: Subject to any disclaimer, the term of this patent is extended or adjusted under 35 U.S.C. 154(b) by 0 days.

(21) Appl. No.: 15/344,467

(22) Filed: Nov. 4, 2016

Related U.S. Application Data

(60) Provisional application No. 62/252,559, filed on Nov. 8, 2015.

(51) Int. Cl.
*A61B 5/08* (2006.01)
*H04B 10/079* (2013.01)
(Continued)

(52) U.S. Cl.
CPC ........ *A61B 5/0816* (2013.01); *A61B 5/02433* (2013.01); *A61B 5/02438* (2013.01); *A61B 5/0803* (2013.01); *A61B 5/0873* (2013.01); *A61B 5/7203* (2013.01); *A61B 5/725* (2013.01); *A61B 5/7278* (2013.01); *H04B 10/0795* (2013.01)

(58) Field of Classification Search
CPC .............. A61B 5/0816; A61B 5/02433; A61B 5/02438; A61B 5/0803; A61B 5/0873; A61B 5/7203; A61B 5/725; A61B 5/7278; A61B 10/0795
See application file for complete search history.

(56) References Cited

U.S. PATENT DOCUMENTS 4,781,195 A 11/1988 Martin
5,713,355 A 2/1998 Richardson et al.
(Continued)

FOREIGN PATENT DOCUMENTS

| WO | 0143624 A2 | 6/2001 |
| WO | 2008109185 A2 | 9/2008 |
| WO | 2016150749 A1 | 9/2016 |

OTHER PUBLICATIONS

Lazaro et al., Deriving respiration from photoplethysmographic pulse width, Med Biol Eng Comput (2013) 51:233-242.*
(Continued)

*Primary Examiner* — Bo J Peng
(74) *Attorney, Agent, or Firm* — RatnerPrestia

(57) ABSTRACT

There is disclosed a respiration rate monitoring system and method using a non-invasive device and method of monitoring it nearly continuously. One aspect includes receiving a series of signal data points from an optical sensor, detecting a series of peaks or valleys for the filtered signal data points, determining the time difference between individual peaks or valleys of the series of peaks or valleys to produce a series of time difference values, detecting peaks or valleys for the series of time difference values, determining widths between the peaks or valleys of the series of time difference values, and estimating a respiration rate from the widths between the peaks or valleys of the series of time difference values, and converting the estimation of a respiration rate to an indicator indicative of a respiration rate.

2 Claims, 5 Drawing Sheets

(51) Int. Cl.
*A61B 5/087* (2006.01)
*A61B 5/00* (2006.01)
*A61B 5/024* (2006.01)

(56) References Cited

U.S. PATENT DOCUMENTS

| | | | |
|---|---|---|---|
| 5,846,190 A | 12/1998 | Woehrle | |
| 5,885,213 A | 3/1999 | Richardson et al. | |
| 5,954,644 A | 9/1999 | Dettling et al. | |
| 6,385,471 B1 | 5/2002 | Mortz | |
| 7,384,398 B2 | 6/2008 | Gagnadre et al. | |
| 7,616,110 B2 | 11/2009 | Crump et al. | |
| 7,740,591 B1 | 6/2010 | Starr et al. | |
| 7,827,011 B2 | 11/2010 | De Vaul et al. | |
| 8,036,842 B2 | 10/2011 | DeVaul et al. | |
| 8,313,439 B2 | 11/2012 | McCombie et al. | |
| 8,378,811 B2 | 2/2013 | Crump et al. | |
| 8,618,930 B2 | 12/2013 | Papadopoulos et al. | |
| 8,866,606 B1 | 10/2014 | Will et al. | |
| 9,135,699 B2 | 9/2015 | Ralovich et al. | |
| 9,396,645 B2 | 7/2016 | Will et al. | |
| 9,489,815 B2 | 11/2016 | TenKate | |
| 9,526,421 B2 | 12/2016 | Papadopoulos et al. | |
| 9,547,977 B2 | 1/2017 | Will et al. | |
| 9,640,057 B1 | 5/2017 | Ross | |
| 9,704,154 B2 | 7/2017 | Xing et al. | |
| 9,773,397 B2 | 9/2017 | Ten Kate et al. | |
| 2010/0016738 A1* | 1/2010 | Addison | A61B 5/02416 600/500 |
| 2012/0078116 A1 | 3/2012 | Yamashita | |
| 2014/0142460 A1 | 5/2014 | Zhang et al. | |
| 2015/0164352 A1 | 6/2015 | Yoon et al. | |
| 2016/0038044 A1 | 2/2016 | Banerjee et al. | |
| 2016/0038061 A1 | 2/2016 | Kechichian et al. | |
| 2016/0174913 A1 | 6/2016 | Somanath et al. | |
| 2016/0213314 A1* | 7/2016 | Zuckerman-Stark | A61B 5/7264 |
| 2016/0360971 A1 | 12/2016 | Gross et al. | |
| 2017/0027511 A1 | 2/2017 | Conner | |
| 2017/0172463 A1 | 6/2017 | Papadopoulos et al. | |

OTHER PUBLICATIONS

International Search Report and Written Opinion for International Application No. PCT/US18/18159, dated May 7, 2018, 7 pages.

Addison et al., "Developing an algorithm for pulse oximetry derived respiratory rate (RRoxi): a healthy volunteer study", J. Clin. Monit Comput, 2012, vol. 26, pp. 45-51.

Image of Sensotrack, downloaded Sep. 25, 2016, 1 page.

Meredith et al., "Photoplethysmographic derivation of respiratory rate: a review of relevant physiology", Journal of Medical Engineering & Technology, 2012, pp. 60-66.

George et al., "Respiration Rate Measurement From PPG SIgnal Using Smart Fusion Technique", International Conference on Engineering Trends and Science & Humanities, 2015, 5 pages.

Burns, "Senso Track Monitors Biometric Health Through Your Ear", downloaded http://www.slashgear.com/sensotrack-monitors-biometric-health-through-your-ear-22351940, Sep. 25, 2016, 8 pages.

Lazaro et al., "Deriving respiration from photoplethysmographic pulse width", Med. Bio. Eng. Comput., 2013, vol. 51, pp. 233-242.

Notice of Allowance for U.S. Appl. No. 14/676,639, dated Jul. 16, 2018, 24 pages.

Final Office Action for U.S. Appl. No. 15/254,880, dated Aug. 27, 2018, 13 pages.

* cited by examiner

NON-INVASIVE WEARABLE RESPIRATION RATE MONITORING SYSTEM

CROSS REFERENCE TO RELATED APPLICATIONS

This application claims the benefit of U.S. application entitled "Continuous Non-Invasive Wearable Respiration Rate Monitoring System," application No. 62/252,559, filed on Nov. 8, 2015; this application is also related to the commonly-owned U.S. application entitled "Apparatus for Ambient Noise Cancellation in PPG Sensors," application Ser. No. 14/674,499, filed on Mar. 31, 2015; "CONTINUOUS NON-INVASIVE WEARABLE BLOOD PRESSURE MONITORING SYSTEM," application Ser. No. 14/675,639, filed on Mar. 31, 2015, both of which claim priority to U.S. provisional patent application Ser. No. 61/973,035, filed on Mar. 31, 2014, all of the above disclosures are incorporated herein by reference for all purposes.

TECHNICAL FIELD

The invention relates in general to photoplethysmographic (PPG) measurement systems and apparatuses using optical sensors, and in particular to non-invasive respiration rate measurement by wearable optical sensing systems.

BACKGROUND INFORMATION

The respiration or respiratory rate (RR) or breathing frequency, is the rate (frequency) of ventilation, that is, the number of breaths (inhalation-exhalation cycles) taken within a set amount of time (typically 60 seconds).

Respiration rates may increase with fever, illness, or other medical conditions. Consequently, respiration rate (RR) is recognized as an important clinical parameter. Respiration rate is typically measured in a number of different ways depending upon the clinical setting. The measurement may be performed continuously, for example using: end-tidal $CO_2$ (ETCO2) monitors, EKG-based trans-thoracic impedance systems, nasal thermistors, abdominal and chest bands. Continuous measurements involve specialized and/or obtrusive equipment and hence RESPIRATION RATE is normally available from these devices only when they have been specified for another clinical purpose. In contrast, manual counting typically used as an intermittent spot check made during patient observation and is not a continuous measurement.

Photoplethysmography or photoplethysmographic (PPG) systems have been used in an attempt to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. PPG systems use non-invasive, electro-optical methods that provide information about the volume of blood flowing in a test region close to the skin of body. For example, a PPG signal may be obtained by illuminating the region of interest of body and reflected or transmitted light. In generating the PPG signal, the wavelength A of a light source on one side is placed in a protrusion, for example a finger and a photo-detector or PPG sensor may be placed to other side of the source to capture the transmitted light.

Typically PPG measurement systems include an optical sensor for an attachment to the tip of patient's appendage (e.g., a finger, earlobe and others). The sensor directs light signals into the appendage where the sensor is attached. Some portion of light is absorbed and a remaining portion passes through patient tissue. The intensity of the light passing through the tissue is monitored by the optical sensor. The intensity related signals produced by the sensor are used to compute blood parameters.

PPG sensor can be used in reflection mode (reflecting off of tissue) or in transmission mode (transmitting through the tissue, such as an ear lobe). Normally, a wavelength A in the near infrared space is used because that wavelength generates the strongest modulation of the signal due to light absorption in the haemoglobin in the blood.

It is commonly believed that respiratory activity may cause the PPG to modulate in three fundamental ways. These are:

(1) Baseline (DC) modulation: Changes in venous return secondary to changes in intrathoracic pressure throughout the respiratory cycle cause a baseline DC modulation of the PPG signal. During inspiration, decreases in intrathoracic pressure result in a small decrease in central venous pressure increasing venous return. The opposite occurs during expiration. As more blood is shunted from the low pressure venous system at the probe site and the venous bed cyclically fills and drains, the baseline is modulated accordingly.

(2) Pulse amplitude modulation: Decreased left ventricular stroke volume, due to changes in intrathoracic pressure during inspiration, leads to decreased pulse amplitude during this phase of respiration.

(3) Respiratory sinus arrhythmia (RSA): This is a variation in heart rate that occurs throughout the respiratory cycle. Specifically, it has been well-documented that heart rate increases during inspiration and decreases during expiration. The presence of RSA is influenced by several factors including age, disease status, and physical fitness. While the precise mechanisms of RSA remain controversial, in general, it seems to be the result of autonomic nervous system activity fluctuation during respiration.

The respiratory components often appear concurrently with a range of other low frequency artifacts due, for example, to patient movement, vasomotion or blood pressure changes.

Exact extraction of respiration information from PPG signals currently requires advanced and complex signal processing capabilities coupled with a full analysis of the character of respiratory modulations within the PPG. Such processing capability is beyond the computational processing power of small wearable and unobtrusive technology.

What is needed, therefore, are devices and methods that can accurately, but relatively simply estimate respiration rate from PPG signals so such devices can continuously monitor respiration rate, but in a non-intrusive and convenient manner. Specifically, methods and devices that use smaller processors implemented in wearable technology need simpler computational methods for estimating respiration rate.

SUMMARY

In response to these and other problems, there is disclosed a respiration rate monitoring system and method using a non-invasive device and method of monitoring it nearly continuously. One aspect may be a method of transforming optical signals into indicators indicative of a respiration rate, the method comprising: receiving a series of signal data points from an optical sensor, detecting a series of peaks or valleys for the filtered signal data points, determining the time difference between individual peaks or valleys of the series of peaks or valleys to produce a series of time difference values, detecting peaks or valleys for the series of time difference values, determining widths between the peaks or valleys of the series of time difference values, and estimating a respiration rate from the widths between the peaks or valleys of the series of time difference values, and converting the estimation of a respiration rate to an indicator indicative of a respiration rate.

More particularly, aspects of the present invention may be a wearable non-invasive respiration rate monitor allowing a mobile and remote reading of respiration rate data from the close proximity as well as from the remote location via the Internet connection.

These and other features, and advantages, will be more clearly understood from the following detailed description taken in conjunction with the accompanying drawings. It is important to note that the drawings are not intended to represent the only aspect of the invention.

DETAILED DESCRIPTION

Specific examples of components, signals, messages, protocols, and arrangements are described below to simplify the present disclosure. These are, of course, merely examples and are not intended to limit the invention from that described in the claims.

When directions, such as upper, lower, top, bottom, clockwise, counter-clockwise, are discussed in this disclosure, such directions are meant to only supply reference directions for the illustrated figures and for orientation of components or in the figures. The directions should not be read to imply actual directions used in any resulting invention or actual use. Under no circumstances, should such directions be read to limit or impart any meaning into the claims.

Figure 1:
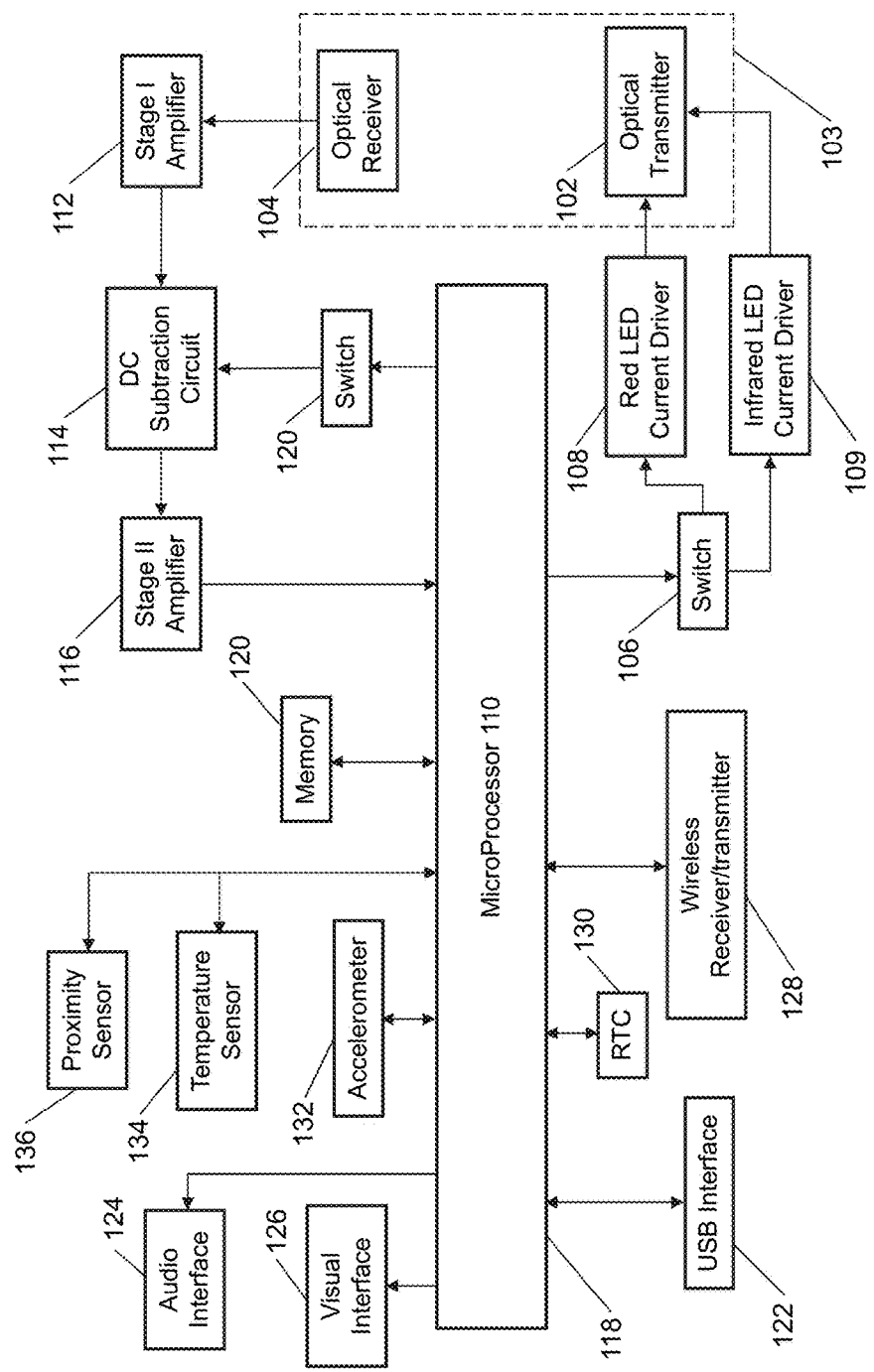
FIG. 1 illustrates a conceptual functional diagram of a vital signs monitoring system incorporating certain aspects of the present invention.

FIG. 1 illustrates a conceptual functional diagram of a vital signs monitoring system 100. The system 100 includes an optical sensor subsystem or pulse oximeter system 103. The optical sensor subsystem 103 is designed to assist in the measurement of a user's vital signs, such as blood pressure, heart rate, respiration rate and oxygen saturation, by using non-invasive methods. For instance, absorption of light by oxyhemoglobin and deoxyhemoglobin are significantly different at red light and infrared light. By measuring the difference in absorbance at various wavelengths, the degree of blood oxygen saturation can be estimated.

The optical sensor subsystem 103 is positioned on a portion of the user's tissue. For instance, the optical sensor subsystem 103 may be mounted on a finger, ear lobe, or a wrist (in a watch worn by the user). The optical sensor subsystem 103 includes an optical transmitter 102, which is designed to transmit light at predetermined wavelengths and an optical receiver 104, adapted to receive the transmitted light from the optical transmitter 102.

In certain embodiments, such as illustrated in FIG. 1A, the optical transmitter 102 and the optical receiver 104 are positioned adjacent to each other so that the optical receiver 104 may receive reflected light from the user's tissue originated by the optical transmitter 102. In other words, the optical transmitter transmits light to penetrate the skin to the blood underneath. Some portion of transmitted light is getting absorbed by the blood, and the remaining portion of it is reflected by the tissue, which is then received by the optical receiver 104.

In other embodiments, such as illustrated in FIG. 1B, the optical receiver 104 is positioned in opposition to the optical receiver 102 such that the optical receiver 104 may receive light that has passed through the skin and goes through the blood (such as when the user's ear lobe is positioned between the optical receiver 102 and the optical receiver 104.)

The intensity of light passing through the tissue is received by the optical receiver 104, which in some embodiments, may be a photodiode. The photodiode generates current from the received light. The greater the light received, the greater the current generated by the photodiode.

The light to be transmitted through the user's tissue is selected to be of one or more wavelengths that are absorbed by the blood in an amount representative of the amount of the blood constituent present in the blood vessel. The amount of transmitted light scattered through or reflected from the tissue will vary in accordance with the changing amount of blood constituent in the blood vessel and the related light absorption.

In certain embodiments, the optical transmitter 102 transmits red light at around a wavelength of 580 to 660 nm via a red LED, and infrared light at around a wavelength range of 880 to 940 nm via an infrared LED. However, a light source having wave lengths from 330 nm to 1200 nm would work for respiration rate determinations. Thus, either wavelength range can be used, in certain embodiments of the present invention, light from the infrared LED are used to determine respiration rate.

Thus, in certain embodiments the optical transmitter 102 comprises two LEDs controlled by a LED controller circuit. In certain embodiments, the LED controller circuit selects the active LED and its current management. In the illustrative embodiment, the LED controller circuit comprises a Digital-to-Analog Converter ("DAC"), a switch 106, a Red LED current driver 108, and an Infrared LED current driver 110. Switching to the active LED may be controlled by the microprocessor 118 via MCU pins, which commutes control voltage from a Digital to Analog Converter ("DAC") to the selected LED at appropriate intervals via the switch 106 and the LED current drivers 108 and 109. As is well known in the art, a DAC converts digital signals to an analog signal such as current or voltage. Such digital signals are usually called PPG signals.

In embodiments that use a single photodiode, the light of different wavelengths, such as red and infrared, is time multiplexed. The detected signal, therefore, should be demultiplexed. The demultiplexing frequency may be high enough so that it is much larger than the pulse rate.

In certain embodiments, the current generated by the optical receiver 104 may be sent to a first stage amplifier 112 to amplify the received current, such as a first stage transimpedance amplifier. The amplified current or output signal from the first stage amplifier 112 comprises a DC component and an AC component. A typical PPG signal consists of the large DC component caused by skin, muscle, and bone not involving blood vessels and a small AC component that represents arterial blood. Typically, this AC component is superimposed onto a large quasi-DC component that relates to the tissues and to the average blood volume. However, respiration causes the DC component to vary slowly.

The "text-book" depiction of the PPG signal used in pulse oximetry for the computation of oxygen saturation (SpO2) is one where a repeating smooth, double-humped, cardiac 'pulse' waveform sits on top of a large constant baseline component (often called the DC component). However, in practice this is often not the case and, in fact, both the cardiac pulse and baseline components can vary quite significantly over time. This variation is caused by a variety of factors including, for example: vasomotion/compliance effects, changes in venous pooling related to heart rate/ cardiac output variations, blood pressure changes and respiratory modulations. In standard pulse oximetry, these variations are commonly filtered out to isolate the cardiac (arterial) pulse component for the purpose of determining SpO2. However, they may be useful for determining respiration.

The AC component represents the change of received light (by the optical receiver 104) and thus the change of blood in the vessel. Also the physiological, ambient and system generated DC component constituting the noise is present in the received light, in other words the blood change in the vessel can be visualized in the form of an AC component accompanied by the noise represented in the form of the DC component. At this stage, only the AC component is the subject of processing.

In some embodiments, a DC subtraction circuit 114 extracts the DC component of the signal and is used as an offset input to the second stage operational amplifier 116. Thus, only the AC portion of the signal is amplified by the second stage amplifier 116.

An A/D converter (not shown) receives the amplified current from the second stage operational amplifier and converts it into a digital waveform which is then sent to a microprocessor 118.

In certain embodiments, the system 100 also includes an ambient noise reduction circuit, which reduces noise due to ambient light effect in the received current using the switch 119. More details regarding the ambient noise reduction circuit is found in the jointly owned and co-pending patent application "Apparatus for Ambient Noise Cancellation in PPG Sensors," application Ser. No. 14/674,499, filed on Mar. 31, 2015, the specification of which has been incorporated by reference into this Application.

The microprocessor 118 receives the digital waveform from the Second Stage Amplifier 116 via the A/D converter as an input signal Although many microprocessors may be used, an ultra low power microprocessor is preferred. In one embodiment, the microprocessor 118 or "MCU" may be based on the 32 bit ARM Cortex-M4 core, which includes a variety of peripheral devices. In certain embodiments, the microprocessor is ultra low power with consumption of about 238 µA/MHz in dynamic run mode, and 0.35 µA in lowest power mode. Although low energy, the core of the microprocessor 118 is powerful enough to allow collection and processing of data from the sensors on the fly.

The microprocessor 118 is coupled to at least one memory 120 for storing post-processed data and for the firmware instructions. In certain embodiments, the memory 120 may be approximately 256 Mb of serial flash memory. In certain embodiments, the microprocessor 118 is also in communication with a USB ("Universal Serial Bus") interface 122, such as a micro USB interface. The USB interface 122 may be coupled to an USB-to-UART ("Universal Asynchronous Receiver and Transmitter") converter (not shown), such as an enhanced UART with an USB interface. Among other features, the USB interface 122 allows the microprocessor 118 to communicate with an external computing device via a wired USB cable. In certain embodiments, the USB interface 122 also supports USB suspend, resume and remote wakeup operations. Program instructions residing in the memory 120 may be updated via the USB interface 122 (e.g., firmware) and where necessary data may be transferred between the microprocessor 118 and the computing device.

The USB interface 122 is also coupled to the system's power supply circuit (not shown) and can receive direct current to charge and recharge a portable power supply, such as a lithium-ion polymer battery (not shown). In some embodiments, the power supply may be coupled to an On/Off controller which is also coupled to a on/off switch. In certain embodiments, the system's power supply can be inductively charged. As such power supply circuits are well known in the art, the power supply circuit will not be discussed in detail in this disclosure.

In certain embodiments, the microprocessor 118 sends control signals to the optical transmitter 102, which begins transmitting light to be received by the optical receiver 104 to start the data gathering process. Additionally, the microprocessor 118 performs data acquisition and analysis on the received digital waveforms the second stage amplifier 116. As will be described below, the microprocessor 118 uses the received digital waveforms to determine calculated results such as blood pressure, heart rate, oxygen saturation, and respiratory rate. The calculated results may be stored in the memory 120 for later transmission or use. The calculated results may also be sent to a number of user interface devices. For example, in certain embodiments, the calculated results may be sent to an audio interface 124 such as an earphone speaker. In other embodiments, the calculated results may be sent to a visual interface 126, such as an LCD display or touch sensitive screen via a display driver (not shown).

Additionally, the calculated results may also be sent to a wireless transceiver 128. In certain embodiments, the wireless transceiver 128 may be a Bluetooth radio capable of communication with a smart phone or other such Bluetooth capable computing device. In certain embodiments, the Bluetooth radio may be a low energy "System on a chip" or "SOC." The SOC may include a microcontroller core with Flash memory and Static RAM. In certain embodiments, the SOC also includes a Bluetooth v4.0 low energy front-end. In certain embodiments, the SOC may be used as a Network processor, which provides Bluetooth Low Energy connectivity. In other embodiments, a ZIGBEE protocol or any other point-to-point wireless protocol (standard or non-standard) may be incorporated into the wireless transceiver.

The microprocessor 118 may also be connected to a number of other system components and peripherals. In certain embodiments, the components may include a Real Time Clock or "RTC" 130, an accelerometer/gyroscope 132, a temperature sensor 134, and/or a proximity sensor 136.

In certain embodiments, a real time clock 130 may be a RTC module with built-in crystal oscillating at 32.768 kHz, 1 MHz Fast-mode Plus (Fm+) two wire I2C interface. Such an RTC module may have a wide interface operating voltage: 1.6-5.5 V, Wide clock operating voltage: 1.2-5.5 V and ultra low power consumption: 130 nA typ @ 3.0 V/25° C.

In certain embodiments, the accelerometer/gyroscope 132 may be an intelligent, low-power, 3/6/9-axis accelerometer/ gyroscope with 12 bits of resolution. In certain embodiments, the accelerometer may be provided with embedded functions with flexible user-programmable options, configurable to two interrupt pins. For instance, embedded interrupt functions enable overall power savings, by relieving the host processor from continuously polling data. There may be access to either low-pass or high-pass filtered data, which minimizes the data analysis required for jolt detection and faster transitions. In certain embodiments, the accelerometer 132 may be configured to generate inertial wake-up interrupt signals from any combination of the configurable embedded functions, enabling the accelerometer/gyroscope 132 to monitor inertial events while remaining in a low-power mode during periods of inactivity.

In certain embodiments, the temperature sensor 134 may be a digital output temperature sensor in a four-ball wafer chip-scale package (WCSP) capable of reading temperatures to resolution of 1° C. In certain embodiments, the temperature sensor 134 has a two-wire interface that compatible with both I2C and SMBus interfaces. In addition, the interface supports multiple devices on the bus simultaneously, eliminating the need to send individual commands to each temperature sensor on the bus. In certain embodiments, the voltage requirements vary between 1.4V to 3.6V.

In some embodiments, the proximity sensor 136 allows the presence of a nearby object to be detected. The proximity sensor 136 may be a self-contained, self calibrating digital IC which projects a touch or proximity field to several centimeters through any dielectric. Certain embodiments may be coupled to a capacitor for operation.

A program application or process in the memory 120 may be executed by the microprocessor 118 which in conjunction with the PPG sensor system 103 can estimate certain physical conditions of the user. For instance, the system 100 can measure blood flow. An increase in blood volume within a tissue will result in an increase in the optical path length, and thus a decrease in the intensity of transmitted light. Because the blood flow is pulsatile in nature, the transmitted light (and the value of the PPG signal from optical sensor) changes with time. Over time, the strength of the received PPG signal (usually current or voltage) can be plotted against time when enough samples are taken. A representative plot for a series of PPG sensor values vs. time is illustrated in FIG. 2.

The derived PPG signal curve (after amplification and analog-digital conversion of initial photodiode signal) may then be subjected to mathematical and numerical transformation processes performed by the microcontroller 118 (filtering, normalization, signal conditioning, etc.) to increase the signal accuracy (and therefore, the accuracy of the PPG curve). However, it is common to invert the waveform or signal curve, such that a reduced transmission of light is illustrated as a positive defection.

Figure 2:
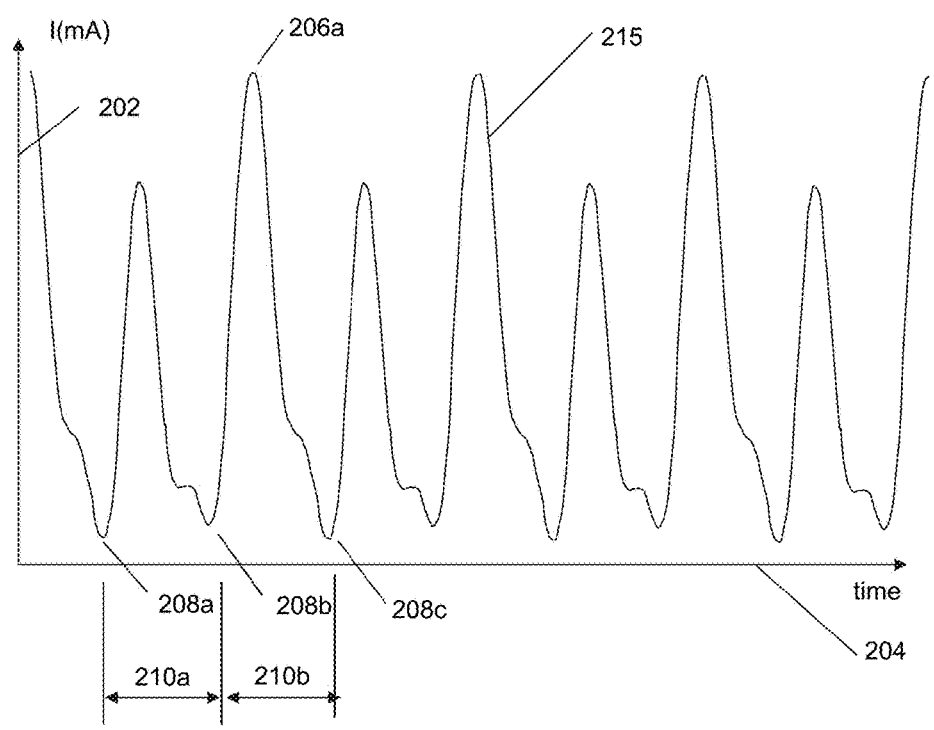
FIG. 2 illustrates an exemplary PPG signal curve graph.

An exemplary PPG signal curve 215 is illustrated in FIG. 2 which illustrates the current (e.g. blood flow plotted as y axis values 202) graphed against a particular period of time (x axis 204). (In some embodiments, the PPG signal curve is inverted to correspond to standard display conventions). Once the PPG signal curve 215 has been received for a particular window or amount of time (t), with the help of a peak and valley curve detector processes (described below), the signal period or pulse width can be measured, the inverse value of which is related to the heart rate. For instance, a peak of the plotted PPG signal 215, such as peak 206a on the signal curve 215, corresponds to high point of blood flow through the tissue. Similarly, a "foot," such as foot 208a, corresponds to the low point of blood flow through the tissue (which can be correlated to zero on the y-axis 204 as illustrated in FIG. 2). As is known, a single pulse represents the rhythmic dilation of the arteries resulting from the beating of the heart. Thus, a single pulse corresponds to the time between peaks or foots (or other recurring events) in the signal curve 215 of FIG. 2. For purposes of illustration, the first single pulse or pulsation 210a can be illustrated as the time between the first foot 208a and the second foot 208b. The second pulse or pulsation 210b is defined as the time between the second foot 208b and the third foot 208c and so on. The pulse rate or heart rate is the number of pulsations measured within a minute.

Figure 3A:
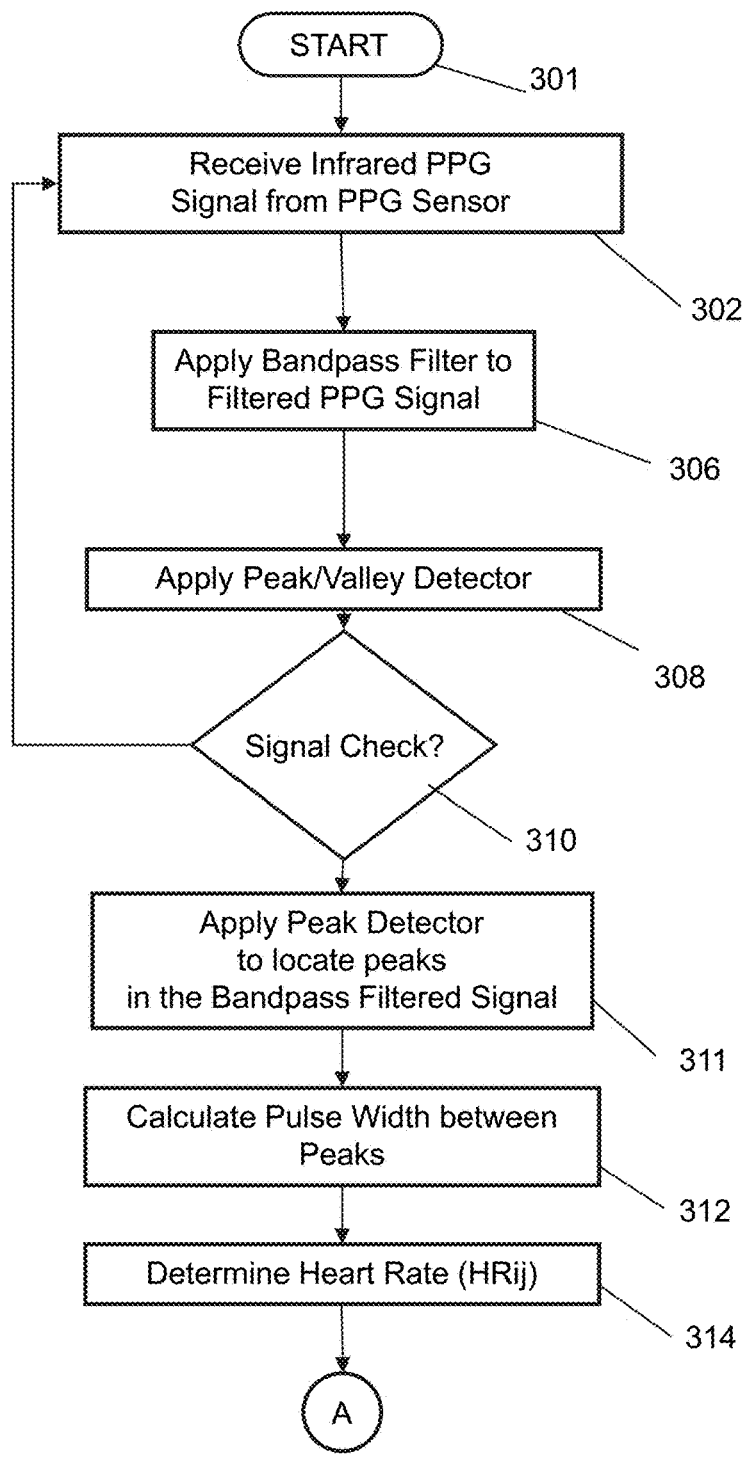
FIGS. 3A and 3B illustrate an overall a process which may be used with certain aspects of the present invention.
Figure 3B:
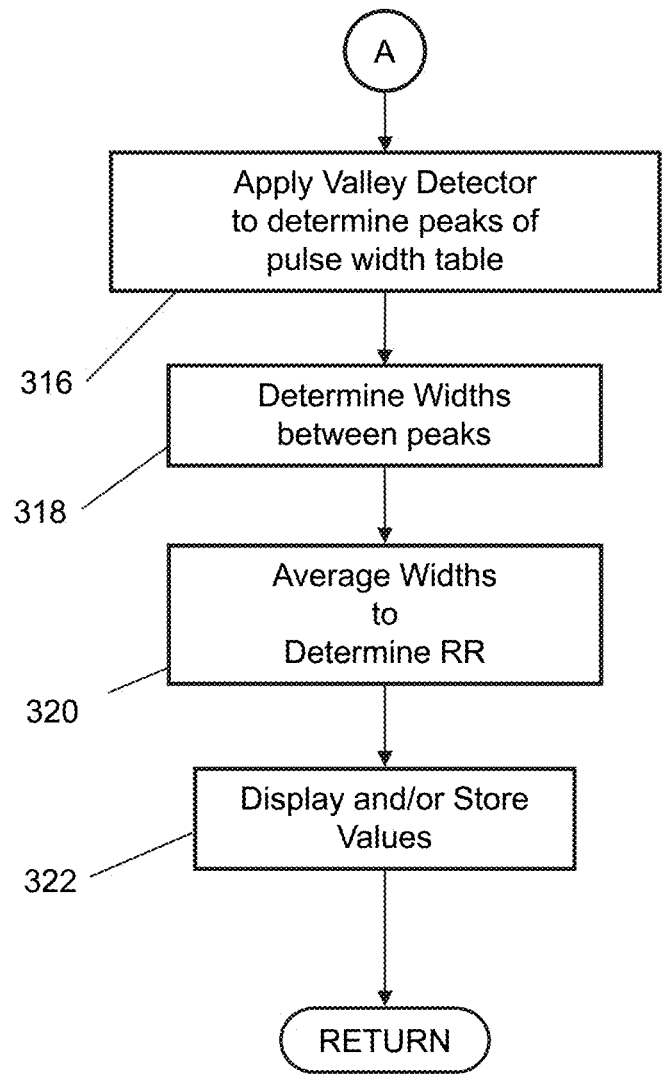

FIGS. 3A and 3B illustrate an overall a process 300 which may be used with certain aspects of the present invention. The basic process 300 starts at step 301 and continues to step 302.

In step 302, data points from the PPG system or sensor are received. For instance, in certain embodiments 512 samples of data points per second from the PPG sensor are received. The individual data points may be stored in a PPG data array representing a PPG signal curve. In certain embodiments, the software equivalent of a moving "analysis window" may be used so that so that previous data points can be used to perform the required analysis while other data points are received.

In step 306, the equivalent of a firmware bandpass filter is applied to the signal from step 302 to create a set of cells or "Q Array" to hold the filtered data points in memory 110. In certain embodiments, a low-pass filter extracts the baseline component (frequencies below the cut-of frequency being let through) and a high-pass filter extracts the pulsatile component (frequencies above the cut-of frequency being let through). In certain embodiments, a 1.75 Hz low pass filter and the standard 4 Hz high pass filter creates a tight band pass which removes much of the noise and artifacts. In certain embodiments, this allows the use of simpler peak/valley determination processes discussed below. In yet other embodiments, the low pass filter may filter lower frequencies, such as 1.5 Hz, 1.0 Hz, 0.75 Hz, and down to 0.5 Hz.

The process then flows to step 308, where a peak/valley detector routine is applied to the filtered "Q Array" (the 0.5 to 4.0 Hz bandpass filtered second stage (OpAmp2) signal) to determine peaks and valleys in the signal (e.g., the peak 206a of the curve 215 of FIG. 2).

The process then flows to step 310 where a signal check is performed. If the received data signal does not meet predetermined signal quality criteria, the process flows to step 302 where new signal values are obtained and the steps 302 to 310 are repeated. On the other hand, if the data signal meets the predetermined signal quality criteria the process flows to step 311. In certain embodiments, the signal quality check may be based on comparing the last 2 valleys with the current peak on the 0.5 to 4.0 Hz bandpass filtered second stage (OpAmp2) signal. A "valid" value is updated for each peak and may be used as a signal check by this and other routines until the next peak is encountered. In certain embodiments, the technique basically turns off most processing for at least one heart beat and turns it on again if it gets at least one good heartbeat. In certain embodiments, sequential peaks are checked, where a second peak has to be between 0.333 and 1.111 times the current or first peak in the window.

The process then flows to step 311; where a peak/valley detector routine is applied to the Q Array (the 1.75 to 4 Hz bandpass filtered data points) to determine peaks and valleys in the signal (e.g., the peak 206a of the curve 215 of FIG. 2). In certain embodiments, this Peak/Valley detector may be a quadratic least squares process peak detectors using consecutive values (e.g.; three) of the filtered Q waveform array.

Once the peaks or valleys have been determined in step 311, the individual pulse widths (e.g., 210a and 210b of FIG. 2) may be determined in step 312, for instance, by just determining the time between peaks.

Using the individual pulse widths, the current heart rate can also be determined in step 314. In one embodiment, the instantaneous HR=60*512/pulse width of the current analysis window and the value is held in memory between peaks for use by other processes. Alternatively, the instantaneous HR can be determined by subtracting the current timestamp for the last peak from the current timestamp and converting the time increments to minutes. For display and other purposes the instantaneous HR may be averaged.

Turning back to FIG. 3A, the graphic match point "A" positioned below step 314 in FIG. 3A indicates that the process connects to the match point "A" of FIG. 3B. Thus, the process flows from step 314 of FIG. 3A to step 316 of FIG. 3B.

In step 316, a peak and valley detector routine is applied to the pulse width values determined from step 312. Graphically this can be represented by FIG. 4 which shows a graph 400 showing the magnitudes of plurality of pulses widths 401 (determined in step 312) charted along the vertical axis 402 against a horizontal axis 404 unit of measurement (such as time). For instance, referring back to FIG. 2, the pulse width distances 210a and 210b of FIG. 2 are now vertical bars in FIG. 4.

Figure 4:
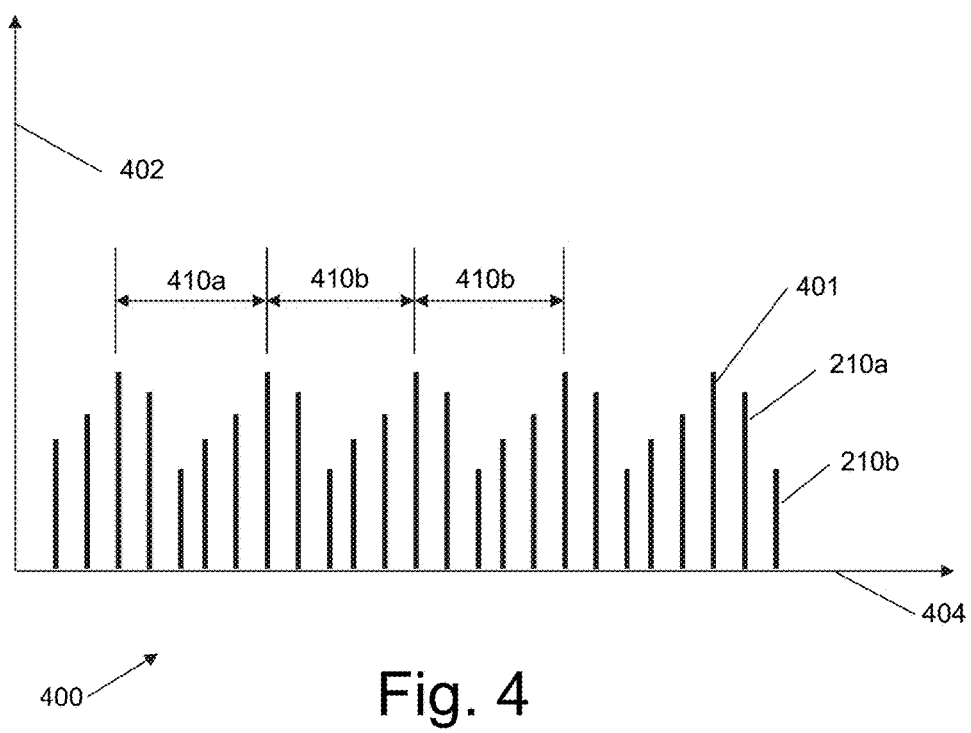
FIG. 4 illustrates a graph of pulse width values.

In certain embodiments, in step 318 a Peak/valley detector routine may then be applied to the plurality of pulse width values 401 of FIG. 4 to determine the width between peaks of the vertical lines (pulse widths of FIG. 2) to produce secondary widths 410a, 410b, 410c, etc. In certain embodiments, this peak/valley detector is a simple V determination process using only 3 consecutive values of the pulse width array. In certain embodiments, this procedure runs at a variable rate based on the heart rate and compares the current value with the previous two values. In other words, the routine is checking the equivalent of PW1>PW2 and PW2<PW3 and comparing the previous pulse width values in an array to the current value.

In certain embodiments; the second set of widths may be stored in a table or an array in memory 120.

In step 320, the width between the second set of peaks within a given analysis window can be averaged. This average can then be correlated to the respiration rate of the user. Mathematically, this can be expressed as:

$$RR = \frac{1}{n}\sum_{i=0}^{n} w_i$$

where w is the individual widths (e.g., 410a, 410b, etc.) between the second set of peaks of the analysis window of the third array and n is the number of peaks in the analysis window.

The respiration rate may then be converted to a rate per minute, displayed on a visual interface, sent to another computer, or stored for later use (step 322).

In some embodiments, a continuous or near continuous respiration rate measurement process may be performed. In such embodiments, the process at step 322 then flows back to step 302 where a new set of PPG signal is received and the process flows to step 306 where the steps 306 through 322 are continuously repeated for as long as the device is on and/or gathering respiration rate signals. In other embodiments, the respiration rate measurement process is only performed at predetermined intervals.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

The invention claimed is:

1. A method of transforming optical signals into indicators indicative of a respiration rate, the method comprising:
    receiving optical signals from an optical sensor;
    transforming the optical signals to a series of signal data points;
    filtering the signal data points to remove data points caused from noise and artifacts;
    checking signal quality of the filtered signal data points by comparing the filtered signal data points against a predetermined signal quality criteria, if the signal quality does not meet the predetermined signal quality criteria, repeating the steps above, if the signal quality meets the predetermined signal quality criteria, proceeding with the steps below;
    detecting a series of peaks or valleys for the filtered signal data points;

determining the time difference between individual peaks or valleys of the series of peaks or valleys to produce a series of time difference values;

detecting peaks or valleys for the series of time difference values;

determining widths between the peaks or valleys of the series of time difference values;

estimating a respiration rate from the widths between the peaks or valleys of the series of time difference values;

converting the estimation of a respiration rate to a indicator indicative of a respiration rate, and storing the estimation of respiration rate in a memory of a device.

2. The method of claim 1, wherein the filtering the signal data points to remove data points caused from noise and artifacts further comprises applying a bandpass filter to the data points.

* * * * *